United States Patent
Matsuo

[11] Patent Number: 6,023,269
[45] Date of Patent: Feb. 8, 2000

[54] IMAGE PROCESSING SYSTEM WHICH STORES A MODIFIED IMAGE AS AN UNMODIFIED SOURCE IMAGE AND MODIFICATIONS THERETO IN SEPARATE FILES

[75] Inventor: Shouichi Matsuo, Urayasu, Japan

[73] Assignee: International Business Machines Corporation, Armonk, N.Y.

[21] Appl. No.: 08/252,730

[22] Filed: Jun. 2, 1994

[51] Int. Cl.[7] .................................................. G06F 15/00
[52] U.S. Cl. .............................................................. 345/333
[58] Field of Search ............................... 395/600, 133, 395/145, 146, 147, 153, 155, 160; 434/117; 345/433, 333

[56] References Cited

U.S. PATENT DOCUMENTS 5,414,809  5/1995  Hogen et al. ............................ 395/155
5,421,012  5/1995  Khoyi et al. ............................ 395/650
5,423,034  6/1995  Cohen-Levy et al. .................. 395/600

Primary Examiner—Phu K. Nguyen
Attorney, Agent, or Firm—Richard M. Ludwin; Ronald L. Drumheller; Louis P. Herzberg

[57] ABSTRACT

A source image and image processing content are stored. If a processed image is requested, the source image is processed according to the processing content and the processed image is displayed. When a source image (unprocessed image) associated with a database is read, a corresponding processed image is displayed according to the processing content stored. An item(s) of processing content instructed to be undone is deleted from the processing content stored, and image processing is then retried according to the processing content after the deletion.

2 Claims, 11 Drawing Sheets

IMAGE PROCESSING SYSTEM WHICH STORES A MODIFIED IMAGE AS AN UNMODIFIED SOURCE IMAGE AND MODIFICATIONS THERETO IN SEPARATE FILES

I. BACKGROUND OF THE INVENTION a. Field of the Invention

This invention relates to a computer-aided image processing system and a related method.

b. Related Art

Client server computing over local area networks (hereinafter abbreviated as LAN) is nowadays steadily spreading in step with the increasing speed and resolution of personal computers. Along with this trend, there is a growing need for image data sharing so that documents can be read with a scanner in the form of image data, which is then stored on a disk of a server and is accessed by a client's personal computer linked to a LAN.

However, it is not desirable that each user processes or modifies shared image data for his/her own purposes. Hence, conventionally in case that there was a need for shared image data to be processed or modified, it was usual to copy corresponding image data onto a client's disk before processing the corresponding image data.

Also in case that a single computer was shared with more than one person, it similarly was usual to store shared source images and processed images on a hard disk or the like. Moreover, in case that a single computer was used by a single user, it was usual to store a source image and its corresponding processed image on a hard disk or the like whenever the user needed both images.

The conventional image processing method has a number of disadvantages. First, the conventional image processing method is disadvantageous in that the amount of image data is much larger than that of text, and hence the storage capacity of a hard disk (a client's hard disk in the case of client server computing) is for a larger part occupied with processed image data. This disadvantage is even more clearly manifest where there are many kinds of processed images to be stored.

Second, inasmuch as image data copied onto a local disk or the like, is not associated with a database even where source images (images stored in a server for client server computing) can be retrieved from a database management system (hereinafter abbreviated as DBMS), the conventional image processing method is disadvantageous in that it disallows retrieval of such image data by a DBMS, and thus only unprocessed images (source images) can be displayed when image data retrieval is performed by a DBMS.

Third, inasmuch as the prior art does not retain a stored copy of original source images when images are processed, there may arise occasions in which it is impossible to restore an image through canceling processing.

II. SUMMARY OF THE INVENTION

Hence, an object of this invention is to provide an image processing system and a related method capable of solving the above-mentioned problems.

In order to attain this object, according to a first aspect an image processing system is provided with image storing means for storing an image; processing instruction inputting means for inputting an image processing instruction; first image processing means for processing an image on (or with) the processing instruction; processing content storing means for storing processing content by the processing instruction in correspondence to the image; second image processing means for processing the image according to the processing content thus stored in the processing content storing means; and processed image displaying means for displaying an image processed by the first or the second image processing displaying means.

According to another aspect, an image processing method includes a processing instruction inputting step for inputting an image processing instruction; a first image processing displaying step for processing an image on (or with) the processing instruction; a second image processing displaying step for processing the image according to the processing content stored by the processing content storing step; and a display step for displaying on a display an image processed by said first or said second image processing step.

According to a third aspect an image processing system is provided with an image file containing a source image to be displayed on a screen; edit processing means for editing said source image on said screen; a transparent sheet file containing a modification made in said source image by said edit processing means; and an edited image displaying means for displaying an edited image through combining said image file with said transparent sheet file.

III. BRIEF DESCRIPTION OF THE DRAWING

IV. DETAILED DESCRIPTION OF THE PREFERRED EMBODIMENTS

Figure 11:
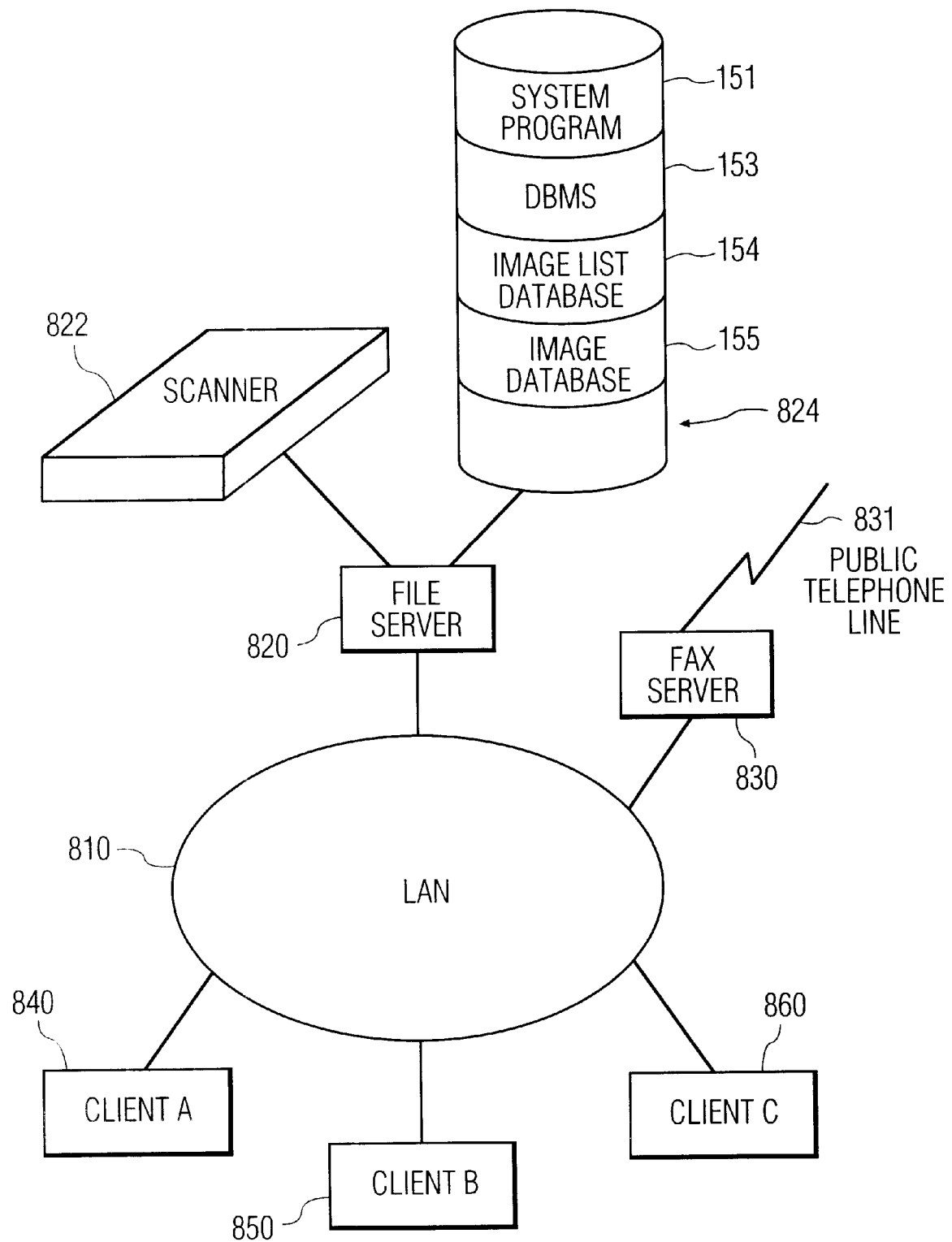
FIG. 11 is a system diagram of the configuration of a client server computing system as an embodiment of this invention.

FIG. 11 is a system diagram of the configuration of a client server computing system as one embodiment of this invention. According to FIG. 11, the client server computing system includes a local area network (LAN) 810 over which clients are connected to a server. The LAN 810 may be IBM Corporation's Token Ring Network (16 Mbps) or Novel Corporation's Netware 386 (Netware is a trademark of Novel Corporation), for example. There are also a file server 820, a FAX server 830, and clients 840 to 860, which are compatible with IBM PS/55 5551-VOB (IBM and PS/55 are trademarks of IBM Corporation, U.S.A.), for example. Although in this embodiment, IBM DOS 4.0 and Microsoft's Microsoft Windows 3.0 (Microsoft and Windows are trademarks of Microsoft Corporation) are mounted in the file server 820, the FAX server 830, and clients 840 to 860, this invention may be applied to computer systems using the other operating systems, such as UNIX (UNIX is a trademark of Unix System Laboratories' developments and licensed products).

The FAX server 830 is connected to a public telephone line 831, such as the public switched telephone network (PSTN) or integrated services digital network. The FAX server 830 transmits FAX image data received over the public telephone line 831 to a file server 820 via a LAN 810 and sends images received from the file server 820 or clients 840 to 860 to the public telephone line 831 via the LAN 810.

The file server 820 is connected to a large capacity external hard disk 824 and an image reading scanner 822. The file server 820 accumulates images received from the FAX server 830 or the scanner 822 on the external hard disk 824. Also, the file server 820 sends an image list or images accumulated on the external hard disk 824 to the LAN 810 by request from clients 840 to 860. The external hard disk 824 accumulates an image database 155, an image list database 154 for storing images together with related information, a database management system (DBMS) 153, and various system programs 151 for operation as server.

Figure 1:
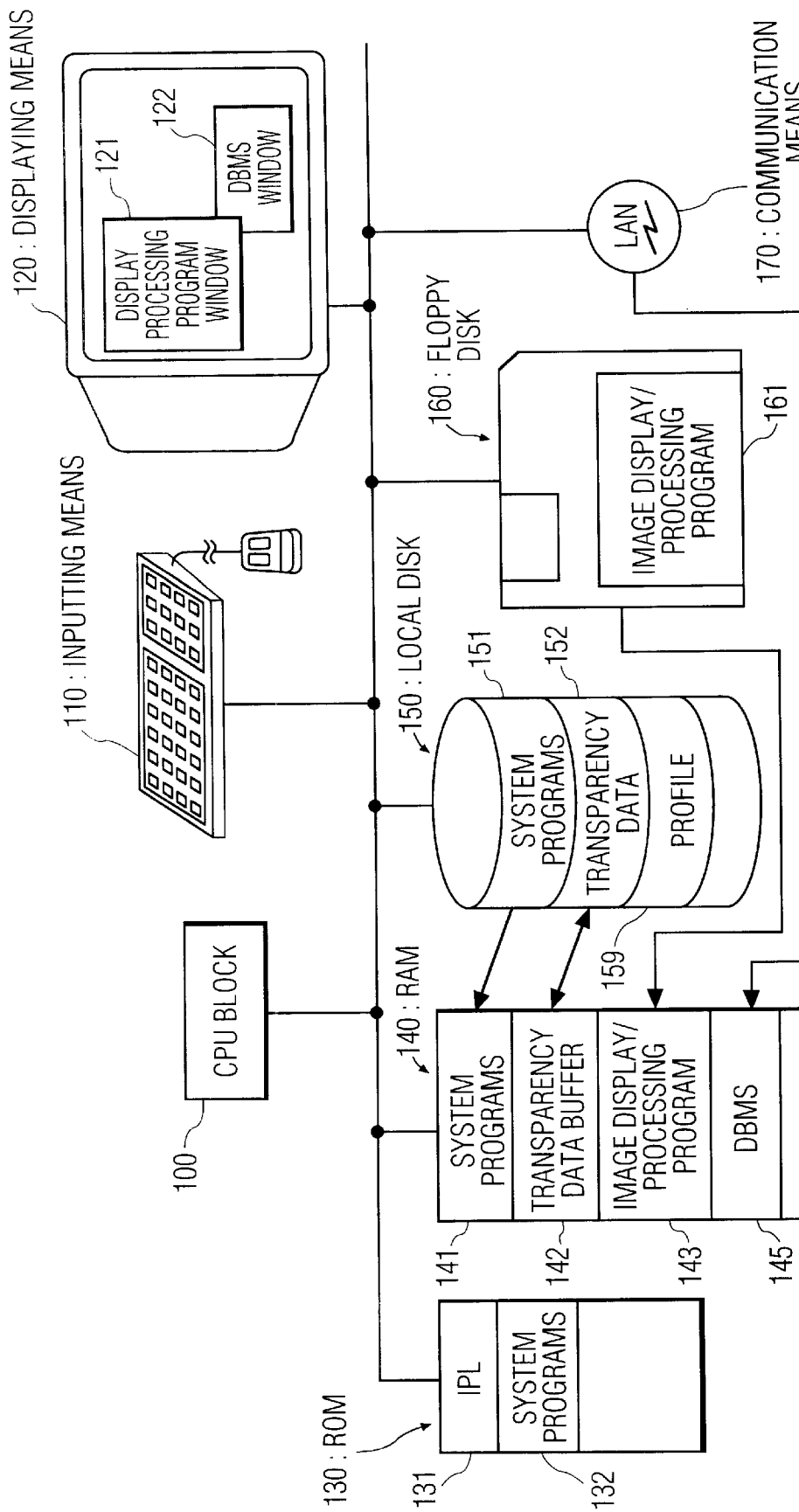
FIG. 1 is a block diagram of an example of a client's hardware in Embodiment 1 of this invention.

FIG. 1 is a block diagram of an example of hardware of clients' 840 shown in FIG. 11. According to FIG. 1, there is a CPU block 100 including a CPU, such as Intel 80386, and a bus controller. There are also inputting means 110, such as a keyboard and a mouse, for input from users and displaying means 120, such as a CRT and an LCD, for visual output to users.

There is also a ROM 130, which stores an initial program loader (IPL) 131 for loading programs into a RAM 140 immediately after POWER ON and other system programs 132. There is also RAM 140, which stores system programs 141, including programs for communication with another computer 820 to 860 over a LAN 810 and programs for control of various inputting/outputting means 110 and 120. There is also a local disk 150, which stores system programs 151 and transparency data 152. The system programs 141 in the RAM 140 are loaded from the local disk 150 at POWER ON. There is also a floppy disk 160, which provides an image display/processing program 161 of this invention in the form of a program stored on floppy disk. This invention can be implemented by installing the image display/processing program 161 first in the local disk 150 and then loading it into the RAM 140 when it is used, or else loading it from a floppy disk 160 directly into the RAM 140. There is also communication means 170 for communication over the LAN 810. The communication means 170 receive from the file server 820 the DBMS 153 stored in the external hard disk 824, an image list retrieved from the image list database 154, and image data 146 selected from the image database 155. The CPU block 100 stores the information thus received in the RAM 140, as shown in FIG. 1.

Figure 2:
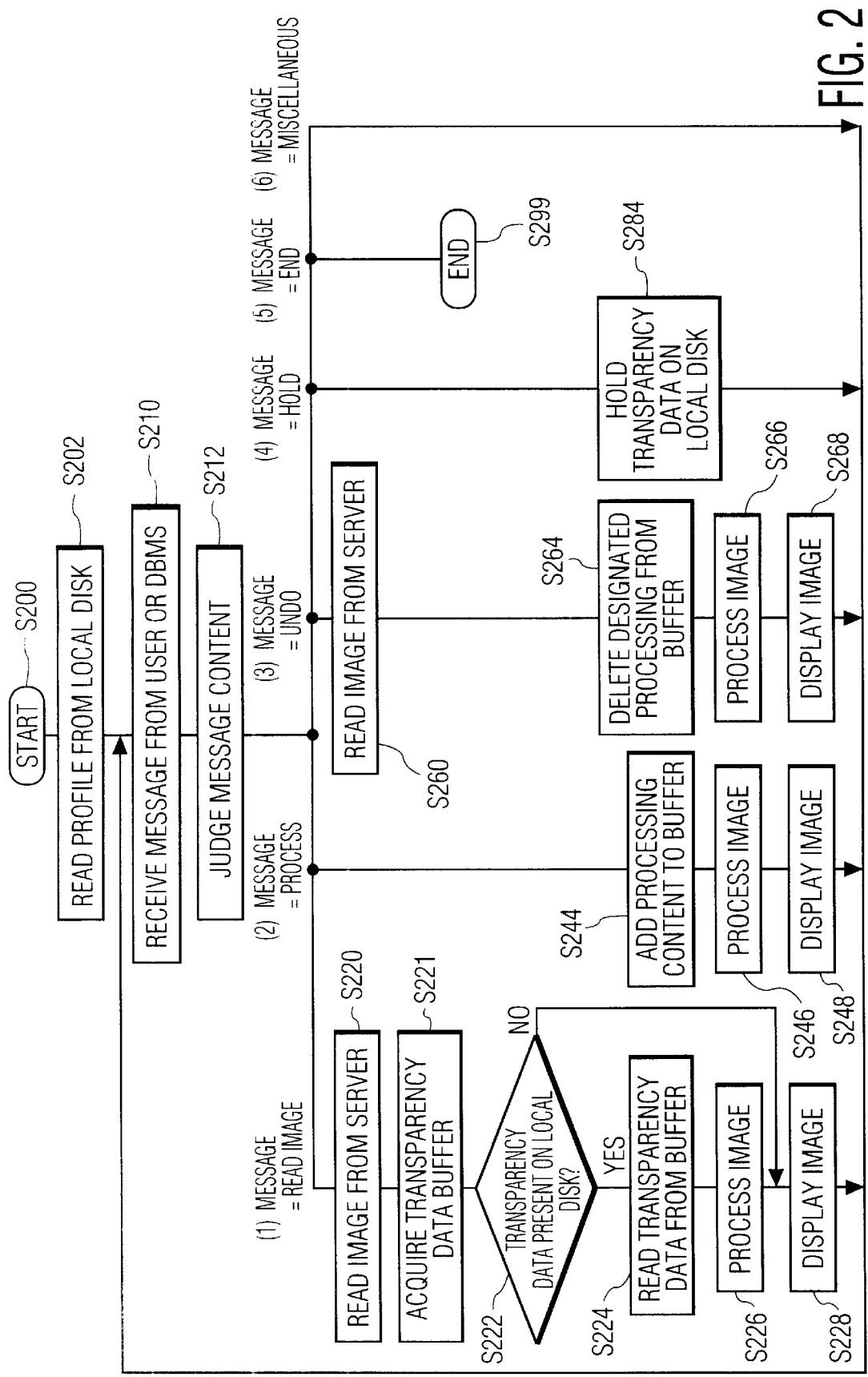
FIG. 2 is a flowchart of the image display/processing program executed by clients in Embodiment 1 of this invention.
Figure 3:
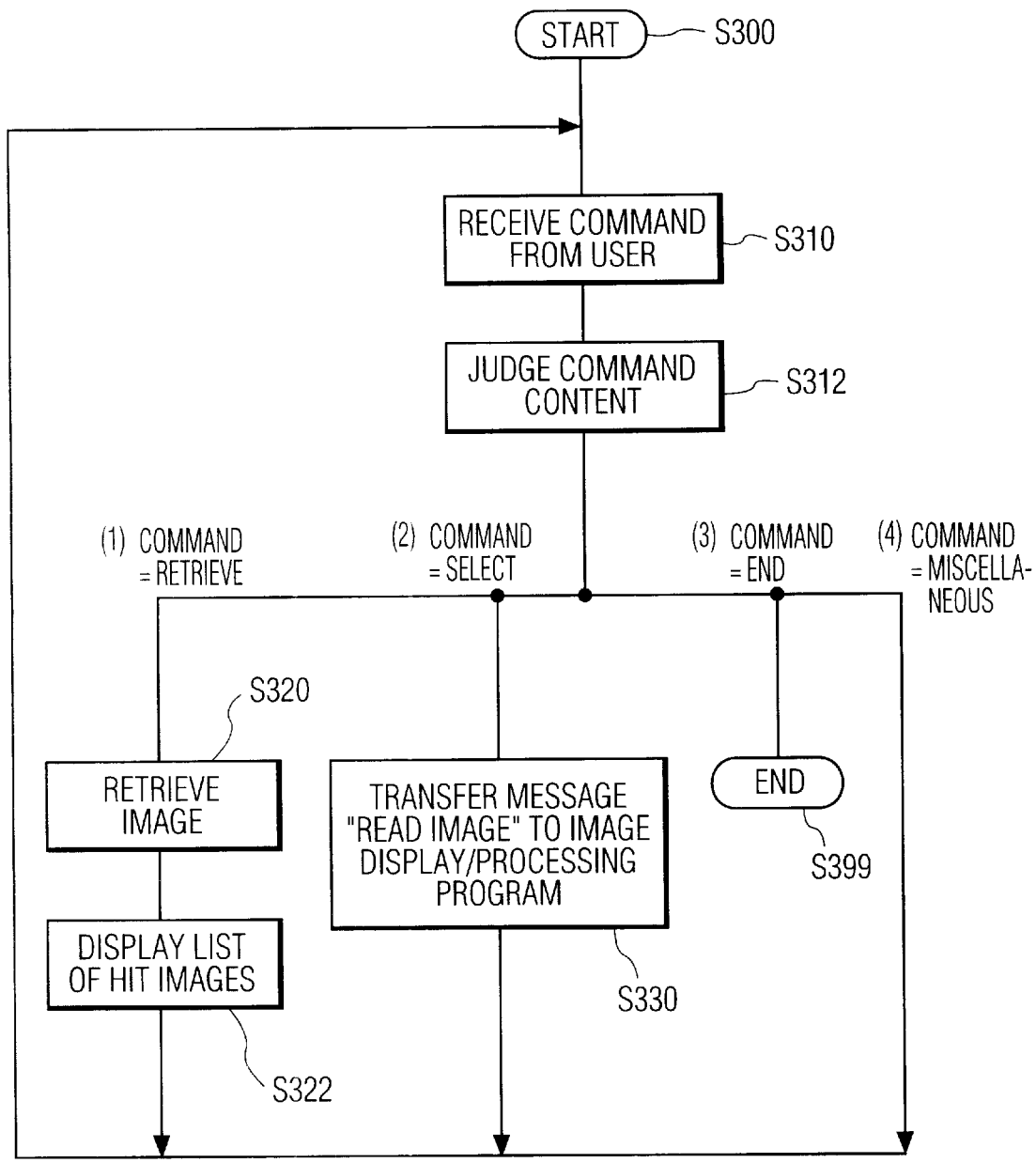
FIG. 3 is a flowchart of the DBMS executed by clients in Embodiment 1 of this invention.

The following describes the operation of the CPU block 100 shown in FIG. 1 with reference to FIGS. 2 and 3. FIG. 2 is a flowchart of the behavior of the CPU block 100 for the image display/processing program 143. FIG. 3 is a flowchart of the operation of the CPU block 100 for the DBMS 145. These two operations are executed in parallel by the functions of system programs 141. Although in this embodiment, IBM DOS4.0 and Microsoft Windows 3.0 are used as means for providing parallel operations, it is also possible to use another multitask operating system, such as UNIX.

According to FIG. 3, when the CPU block 100 starts the operation of the DBMS 145 (at step S300), a DBMS window 122 is first displayed on the displaying means 120. Then, a command from a user to the DBMS is received (at step S310) and its content is judged (at step S312). (1) If the input command is RETRIEVE, then image retrieval is performed according to the retrieval condition designated by the user (at step S320). A list of images which hit the retrieval condition is displayed on the DBMS window 122, and control then returns to step S310. (2) If the command input at step S312 is SELECT, the message "READ IMAGE" and the file name of an image selected are transferred to the image display/processing program (at step S330) and then control returns to step S310. (3) If the command input at step S312 is END, the DBMS window 122 is closed to terminate the operation (at step S399). If the command input at step S312 is not RETRIEVE, SELECT or END, control returns to step S310.

Figure 4:
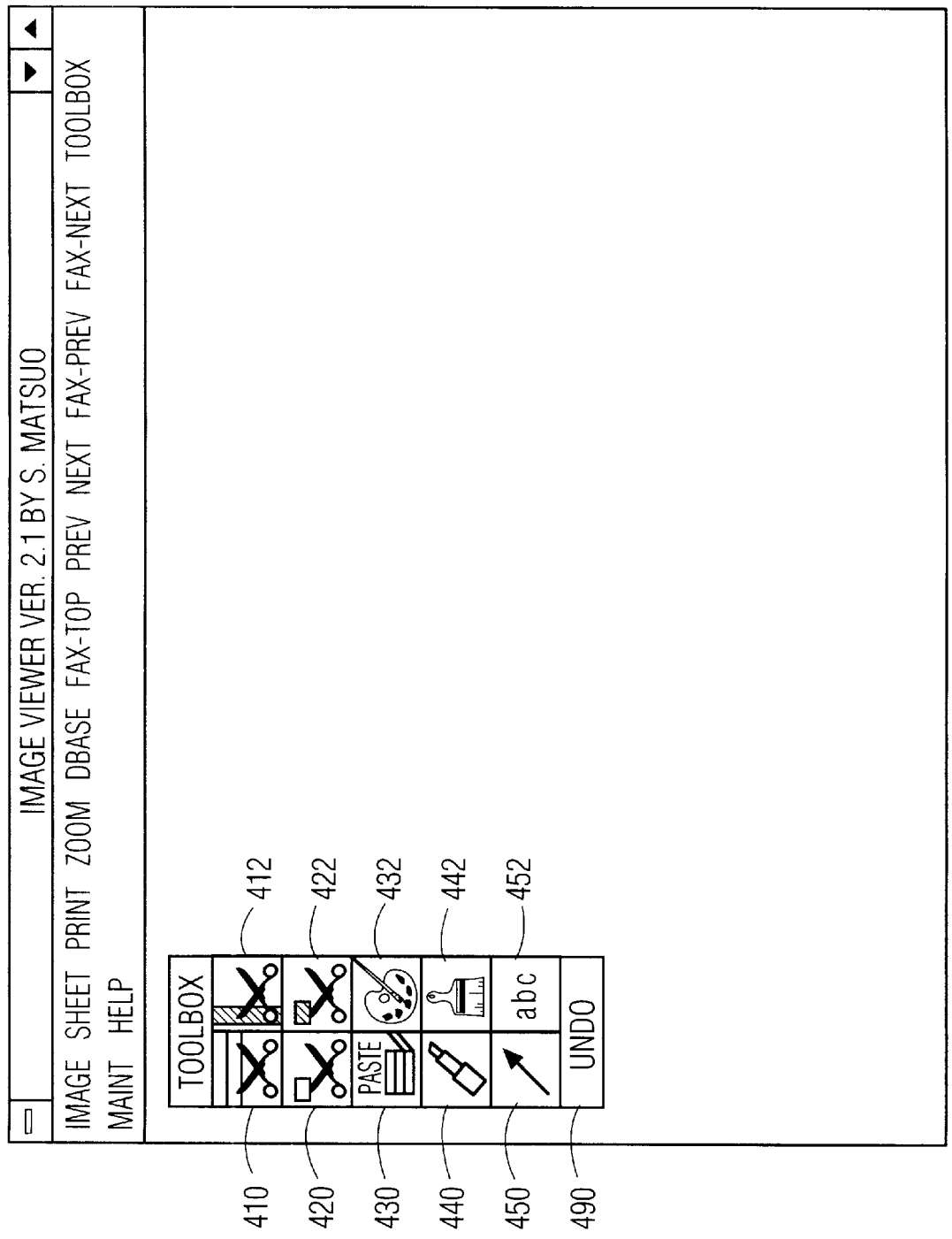
FIG. 4 is an explanatory drawing of a display on the display/processing program window after the end of step 202 shown in FIG. 2.

According to FIG. 2, when the CPU block 100 starts the operation of the image display/processing program 143 (at step S200), a profile 159 containing the drive name of a hard disk to store transparency data and the drive name of a file server 820 is read from the local disk 150 (at step S202). FIG. 4 shows an example of such a display/processing program window 121 after the end of step S202. The CPU block 100 stands by until a message is received from the DBMS 145 as a result of a user's inputting a message with the inputting means 110 or the operation of step S210 shown in FIG. 2.

Figure 5:
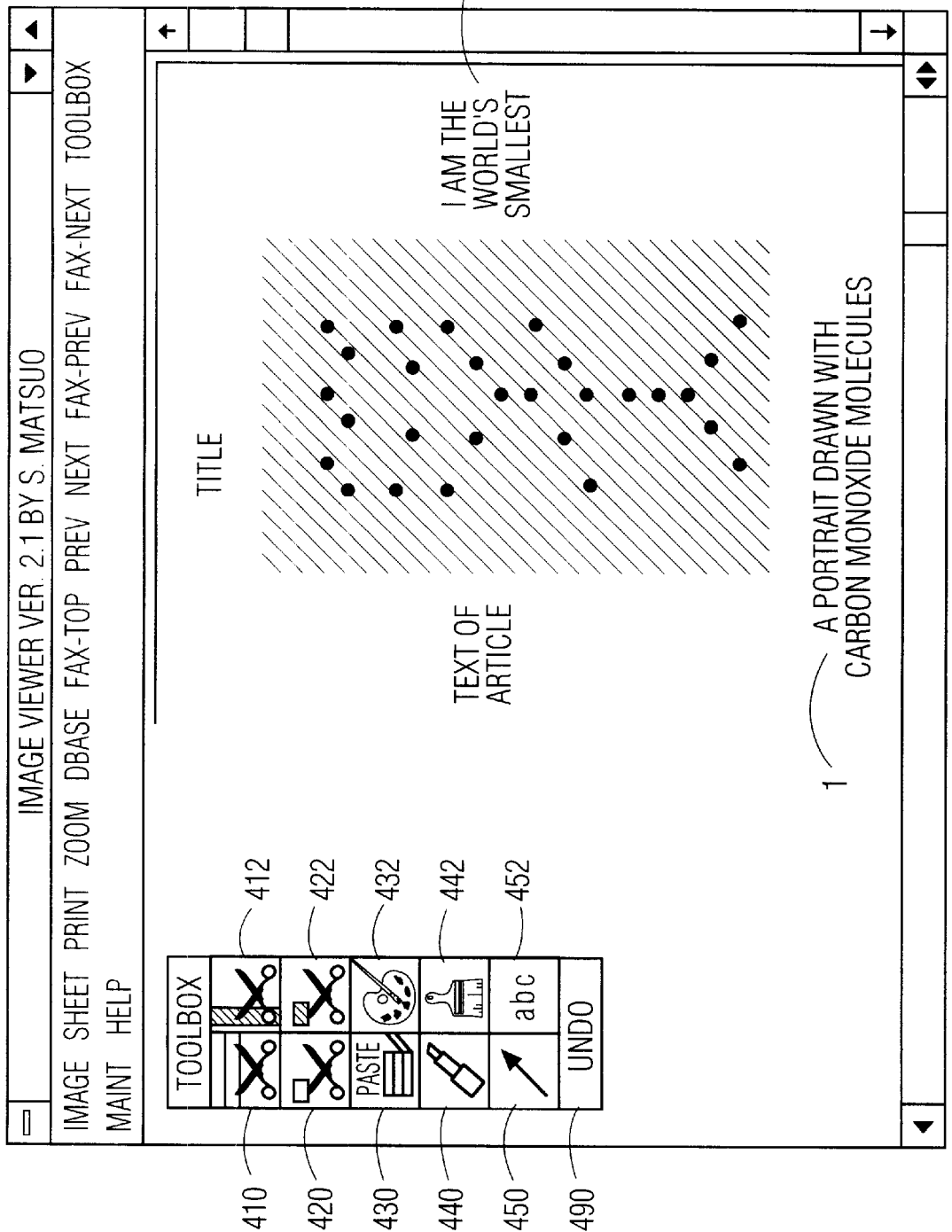
FIG. 5 is an explanatory drawing of a display on the display/processing program window after the end of step 228 shown in FIG. 2.

(1) If a message is input, the CPU block 100 judges its content (at step S212) and reads an image with a designated file name from the file server 820 if the message input is "read image" (at step S220). Then the CPU block 100 reserves a transparency data buffer 142 for storing image processing content (at step S221). At step S222, the CPU block 100 judges whether or not there is transparency data 152 including processing content for the image with the designated file name in the local disk 150. If any transparency data 152 is present, the data is read into the transparency data buffer 142 (at step S224). At step S226, an image read from the server is processed according to the contents of the transparency data buffer 142. At step S228, the image thus processed is displayed on the display/processing program window 121. At step S222, if it is judged that no transparency data 152 is present on the local disk 150, the image read from the server is displayed as is, skipping steps S224 and S226 (at step S228). FIG. 5 shows an example of a display on the image display/processing program window 121 when an image of a newspaper article without any corresponding transparency data is read.

(2) If it is judged at step S212 that the message "PROCESS IMAGE" is displayed, the corresponding processing content is added to the transparency data buffer 142 (at step S244), a designated image is processed (at step S246), and the image thus processed is displayed on the image display/processing program window 121 (at step S248).

The following describes an example of image processing performed at step S246:

(1) Color line marker

If an image range is designated after the color line marker icon 440 displayed under the tool box is clicked with a mouse, the image within the designated range is marked in the color of a palette or changed to the color of a palette.

An image range is designated by pressing the button of the mouse at one point on the image and then releasing the button at a second point, whereby a rectangular range having vertically opposite angles at the first and second points can be designated.

(2) PAINT

If an image range is designated after the PAINT icon 442 is clicked, the designated range will be painted in the color of a palette.

(3) ARROW

If an image range is designated after the ARROW icon 450 is clicked, an arrow mark will be drawn from said first point toward said second point.

(4) CHARACTER

If a character is entered after the CHARACTER icon 452 is clicked and a point on the image on display is selected with a mouse, the entered character will be drawn in the color of a palette on the right-hand side of the designated point. If the leftward or rightward arrow is pressed before a button of the mouse is pressed or the RETURN key is pressed, the entered character will contract or enlarge.

(5) PATCH

If an image range is designated after the PATCH icon 410 or 412 is clicked, the columns or rows where the designated range occurs will be cut out and the rest of the image, exclusive of the columns or rows thus cut out, will be patched up into a new image.

(6) COPY

If an image range is designated after the COPY icon 420 is clicked, the image within the designated range will be copied onto the clipboard (a buffer provided in the RAM 140 for temporary storage).

(7) CUT

If an image range is designated after the CUT icon 422 is clicked, the image within the designated range will be copied onto the clipboard and will then be erased. The erasure is effected by painting the designated range in the same color as is predominant on the periphery of the designated range, for instance.

(8) PASTE

If a button on the mouse is pressed on an image after the PASTE icon 430 is clicked, the contents of the clipboard will be displayed on the lower right side of the point where the button of the mouse has been pressed, and the outer frame of the displayed contents will be drawn. If the rightward or leftward cursor key is then pressed on the inputting means 110, the image on the clipboard will contract or enlarge respectively. If the button of the mouse is released, the outer frame will be erased.

(9) PALETTE

Whenever the PALETTE icon 432 is clicked, the palette changes from one color to another.

In the above processing operations, an image can be "copied" by executing (8) the PASTE command after (6) the COPY command. Also, an image can be "moved" by executing (8) the PASTE command after (7) the CUT command.

At step S244 shown in FIG. 2, the processing instructions for the icons clicked and ranges designated in the course of image processing described in reference to FIG. 5 are added in sequence to the transparency data buffer 142.

However, this "addition of processing content to the buffer" has the following disadvantages: data is accumulated in the transparency data buffer 142 although an image itself undergoes no change if the palette is only clicked; and previous data stored on the clip board is lost once (6) the COPY command or (7) the CUT command is executed. Hence, if (6) the COPY command is executed twice or (7) the CUT command is executed after (6) the COPY command and also (8) the PASTE command is not executed in the meantime, no image is changed by the first COPY command. Nevertheless, at step S244, data is accumulated in the transparency data buffer 142 by the first COPY command.

The accumulation of such useless data is disadvantageous in that it wastes storage space and lengthens processing time for image reproduction.

To offset these disadvantages, the processing content listed in Table 1 may be added to the transparency data buffer 142 in place of step S244.

TABLE 1

| Processing number | Processing content |
|---|---|
| 1 | Draw a color marker in a designated color across a designated range. |
| 2 | Paint a designated range in a designated color. |
| 3 | Write an arrow in a designated color in a designated position. |
| 4 | Write a character in a designated color in a designated position. |
| 5 | Cut out a designated column or row. |
| 6 | Move a designated range to a designated position at a designated magnification. |
| 7 | Copy a designated range to a designated position at a designated magnification. |

The items of processing content corresponding to processing numbers 1 to 5 in Table 1 are added to the transparency data buffer 142 when processing items (1) to (5) are conducted as has been described with reference to FIG. 5.

The processing corresponding to processing numbers 6 and 7 is conducted in the following procedure, for instance:

First, an image is retained on the clip board and a designated range is stored in the RAM 140 when (7) the CUT or (6) COPY command is executed. Also, the processing done last during (7) the CUT, (6) COPY, or (8) PASTE operation is stored in the RAM 140.

Next, when (8) the PASTE command is executed, said processing done last is referenced. If the processing done last is (6) COPY or (8) PASTE, the COPY item corresponding to processing number 7 is added to the transparency data buffer 142. If the processing done last is (7) CUT, the MOVE item corresponding to processing number 6 is added to the transparency data buffer 142.

Similarly, when (6) the COPY or (7) CUT command is executed, said processing done last is referenced from the RAM 140. If the last processing is (7) CUT, the image within the corresponding cutting range is erased or the PAINT item corresponding to processing number 2 is added to the transparency data buffer 142, because the image data on the clip board created by the immediately preceding cutting operation is lost once (6) the COPY or (7) CUT command is executed.

If the processing is (9) PALETTE, no processing content is added to the transparency data buffer 142, because no image is altered by that means alone.

Table 2 shows an example of a data format in which processing content is added to the transparency data buffer 142. Also, Table 3 lists the details of each parameter listed in Table 2.

TABLE 2

| Word Processing number | 1 | 2 | 3 | 4 | 5 | 6 | 7 | 8 | 9 | ... | N + 7 | N + 8 |
|---|---|---|---|---|---|---|---|---|---|---|---|---|
| 1 | PN | CL | X1 | Y1 | X2 | Y2 | | | | | | |
| 2 | PN | CL | X1 | Y1 | X2 | Y2 | | | | | | |
| 3 | PN | CL | X1 | Y1 | X2 | Y2 | | | | | | |
| 4 | PN | CL | X1 | Y1 | X2 | Y2 | SZ | C1 | C2 | ... | CW | 00 |
| 5 | PN | Dummy | X1 | Y1 | X2 | Y2 | | | | | | |
| 6 | PN | CL | X1 | Y1 | X2 | Y2 | PT | X3 | Y3 | | | |
| 7 | PN | CL | X1 | Y1 | X2 | Y2 | PT | X3 | Y3 | | | |

TABLE 3

| | |
|---|---|
| PN | Processing number |
| CL | color |
| X1, Y1, X2, Y2 | Coordinates of image before being processed |
| X3, Y3 | Coordinates of image after being processed |
| SZ | Character size |
| Dummy | Dummy (invalid data) |
| PT | Image enlargement/contraction magnification |
| C1, C2, ... , CN | Character |

As listed in Table 3, PN denotes a processing number, which is a number from 1 to 7. CL denotes the color of a palette put in when the corresponding processing is carried out, thus: 0 if white, 1 if black, and 6 if red. X1 and Y1 are the coordinates of said first point, and X2 and Y2 the coordinates of said second point, used for the designation of an image range. X3 and Y3 are the coordinates of a paste position designated with a click of the mouse. SZ denotes character size, thus: the actual size of a character as against 48 in standard size, for instance. Dummy denotes invalid data whose value is meaningless. PT denotes the enlargement/contraction magnification of a copied or moved image as against a source image. This value can be determined by dividing the width of a copied or moved image by the width of a corresponding source image.

Figure 6:
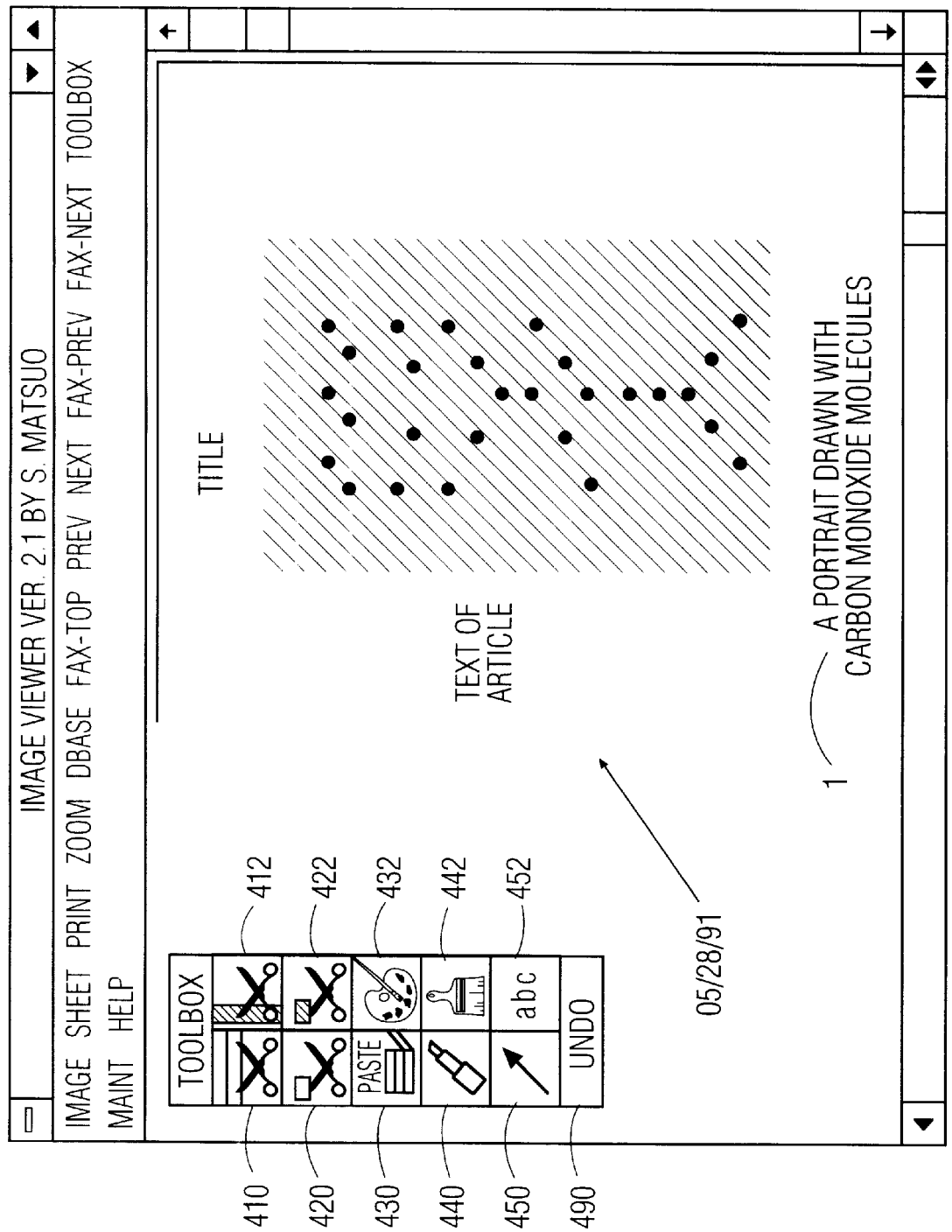
FIG. 6 is an explanatory drawing of a display on the display/processing program window after the end of step 248 shown in FIG. 2.

FIG. 6 is an example of a display on the display/processing program window 121 after the end of step S248. In this example, the following processing has been performed on the source image shown in FIG. 5:

(1) Paint a red line under the message "a portrait drawn with carbon monoxide molecules" (reference numeral 1) at the bottom.

(2) Delete the message "I am the world's smallest" (reference numeral 2) on the right-hand side.

(3) Enter the character string "05/28/91."

Draw an arrow from "05/28/91."

These processing items are represented by the object codes listed in Table 4 in the formats listed in Table 2.

TABLE 4

| Processing Item | Object code | | | | | | | | | | | | | |
|---|---|---|---|---|---|---|---|---|---|---|---|---|---|---|
| 1 | 0002 (PAINT) | 0006 (CL = red) | 0223 (X1) | 0211 (Y1) | 037A (X2) | 0217 (Y2) | | | | | | | | |
| 2 | 0002 (PAINT) | 0000 (CL = white) | 0365 (X1) | 0080 (Y1) | 0390 (X2) | 01F0 (Y2) | | | | | | | | |
| 3 | 0004 (CHARACTER) | 0001 (CL = black) | 0155 (X1) | 0185 (Y1) | 019F (X2) | 019C (Y2) | 0017 (SZ) | 0030 (0) | 0035 (5) | 002F (/) | 0032 (2) | 0038 (8) | 002F (/) | 0039 (9) | 0031 (1) | 0000 |
| 4 | 0003 (Arrow-marked color line) | 0001 (CL = black) | 0170 (X1) | 017A (Y1) | 01DA (X2) | 0145 (Y2) | | | | | | | | |

Thus, the object codes listed in Table 4 have been accumulated in the transparency data buffer 142 when the image shown in FIG. 6 is obtained.

(3) If it is judged at step S212 that the processing of a message is to be canceled or undone, a corresponding source image is read again from the file server 820 (at step S260). Subsequently, the processing item thus designated to be undone is deleted from the transparency data buffer 142 (at step S264). The source images are then processed all over again in sequence (at step S266), and the image thus processed are displayed (at step S268).

The reason why the UNDO command is performed not on the immediately preceding image but on the source image is as follows: if the processing item to be undone is the deletion of image information, e.g., the deletion of designated rows or the contraction of an image, such an "undone" image cannot be reproduced by processing only the image immediately preceding the image to be undone.

Yet, if the processing item to be undone does not entail a reduction of image information, as in drawing a marker, the UNDO command may be performed on the image immediately before being undone, e.g., the deletion of a marker may be carried out. This method has the effect of allowing UNDO processing to be performed at high speed.

It is also possible to have an image read from the server at step S220 temporarily stored on the local disk 150 or the RAM 140, and have the image that has been thus temporarily stored copied onto the image data 146 in the RAM 140.

This method produces the effect of preventing loads on the file server 820 and the LAN 810 from increasing, as well as the effect of enabling UNDO processing to be achieved at high speed.

Figure 7:
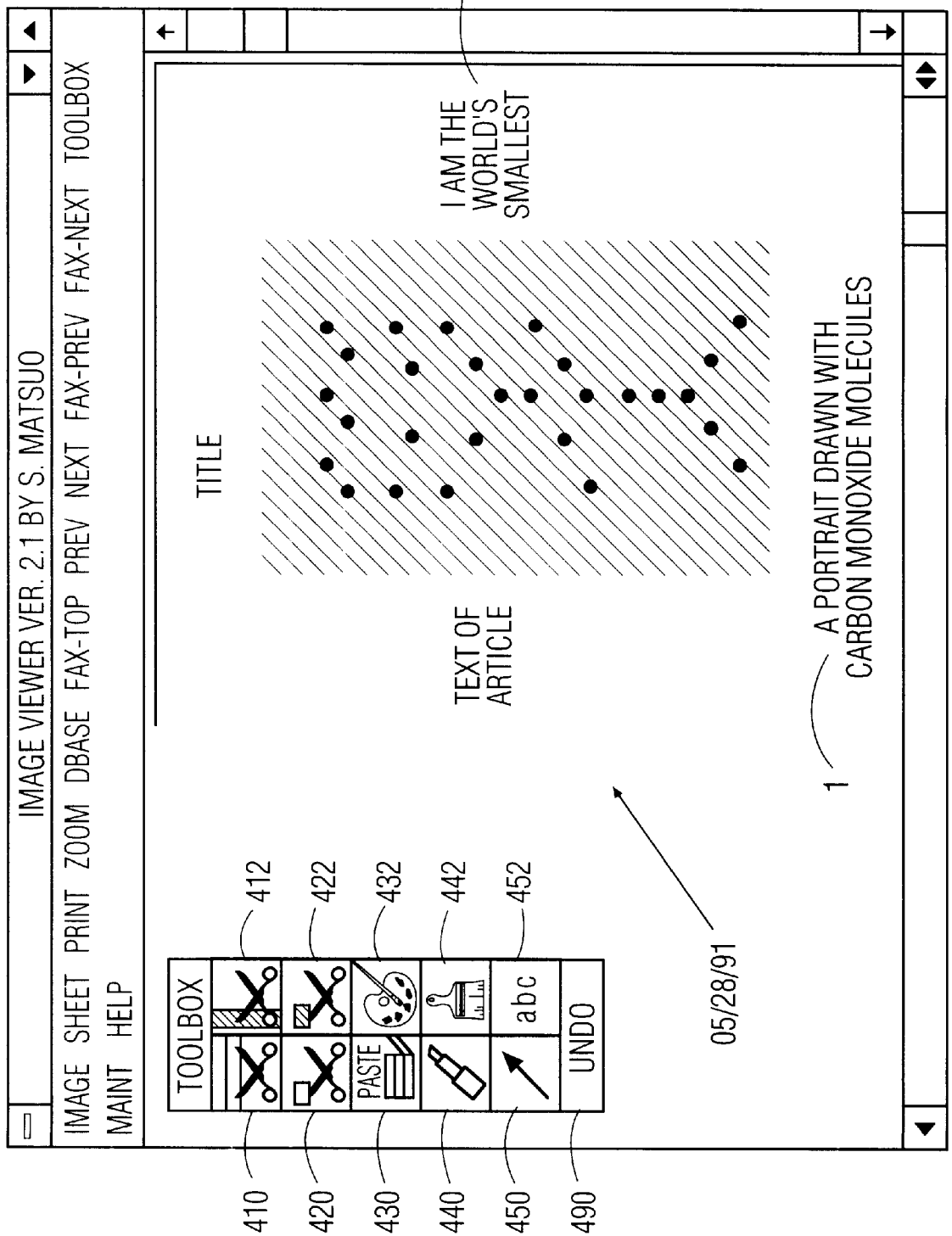
FIG. 7 is an explanatory drawing of a display on the display/processing program window after the end of step 268 shown in FIG. 2.

FIG. 7 shows an example of a display on the display/processing program window 121 after the end of step S268, wherein the following processing on the image shown in FIG. 6 is canceled (undone):
(2) Delete the message "I am the world's smallest" (reference numeral 2) on the right hand side.

Thus, the contents of objects stored in the transparency data buffer 142 after the UNDO operation will be as listed in Table 5 as a result of deleting the second row of Table 4.

In Embodiment 2, by contrast, it is intended that more than one processed image be held.

Inasmuch as the basic system configuration of Embodiment 2 is similar to that of Embodiment 1, FIGS. 1 to 7, FIG. 11, and the explanations about these figures will be quoted also in the description below, wherein only aspects that differ, that is, only steps S284 and S222 in FIG. 2, will be described in detail below.

Figure 8:
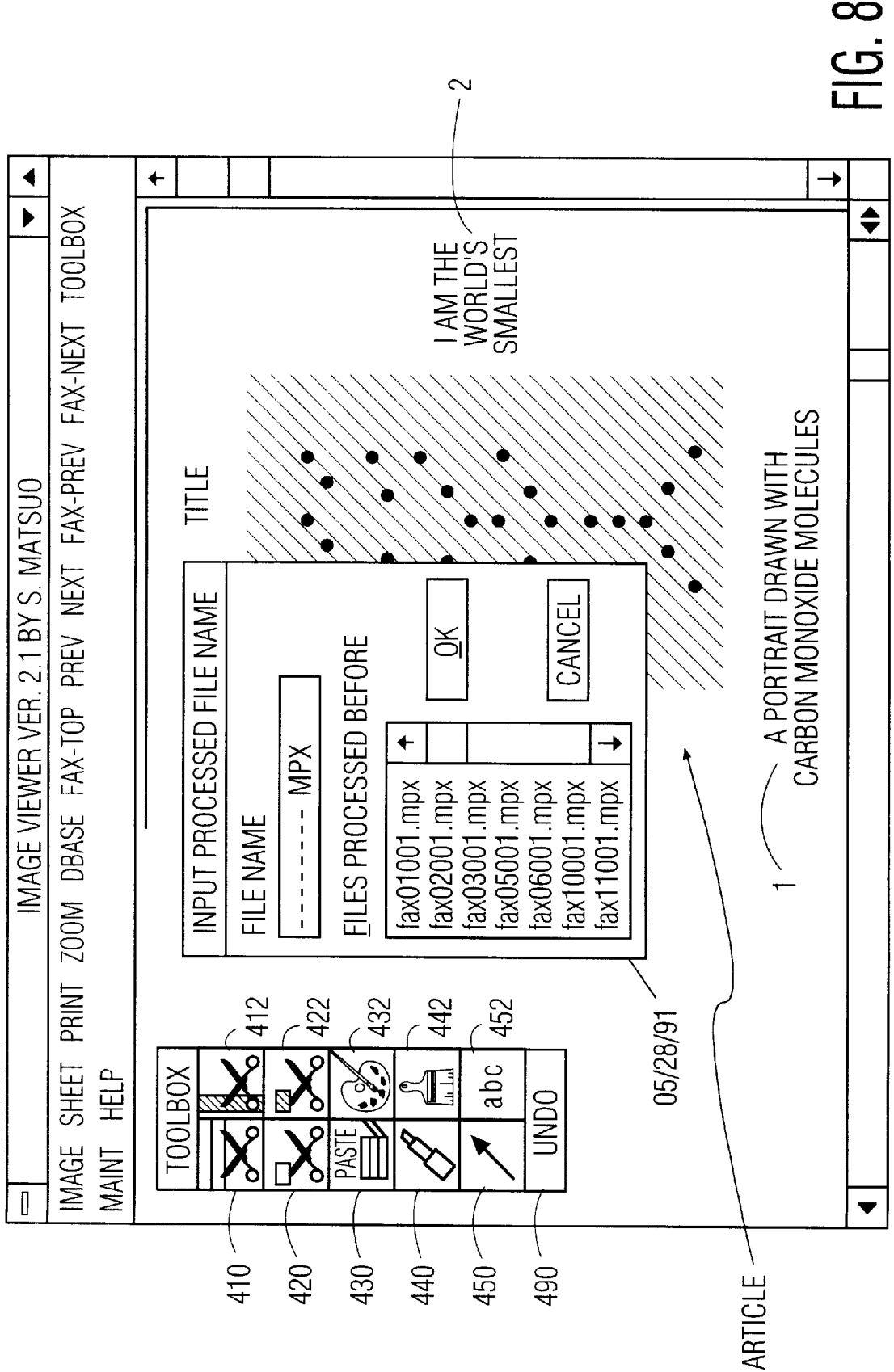
FIG. 8 is an explanatory drawing of a display on the display/processing program window when a file is saved under an alias at step 284 shown in FIG. 2.

The following describes operations to be performed instead of step S284 in FIG. 2 with reference to FIG. 8. As FIG. 8 shows, the CPU block 100 inputs the title of a processed image and stores the contents of the transparency data buffer 142 in a file with the extender MPX (called an MPX file). Then the directory and file name of said MPX file are additionally written into an MAP file with the extender MAP of the directory and file name of a source image. If no MAP file is existent on the local disk 150, it should be created in advance.

Figure 9:
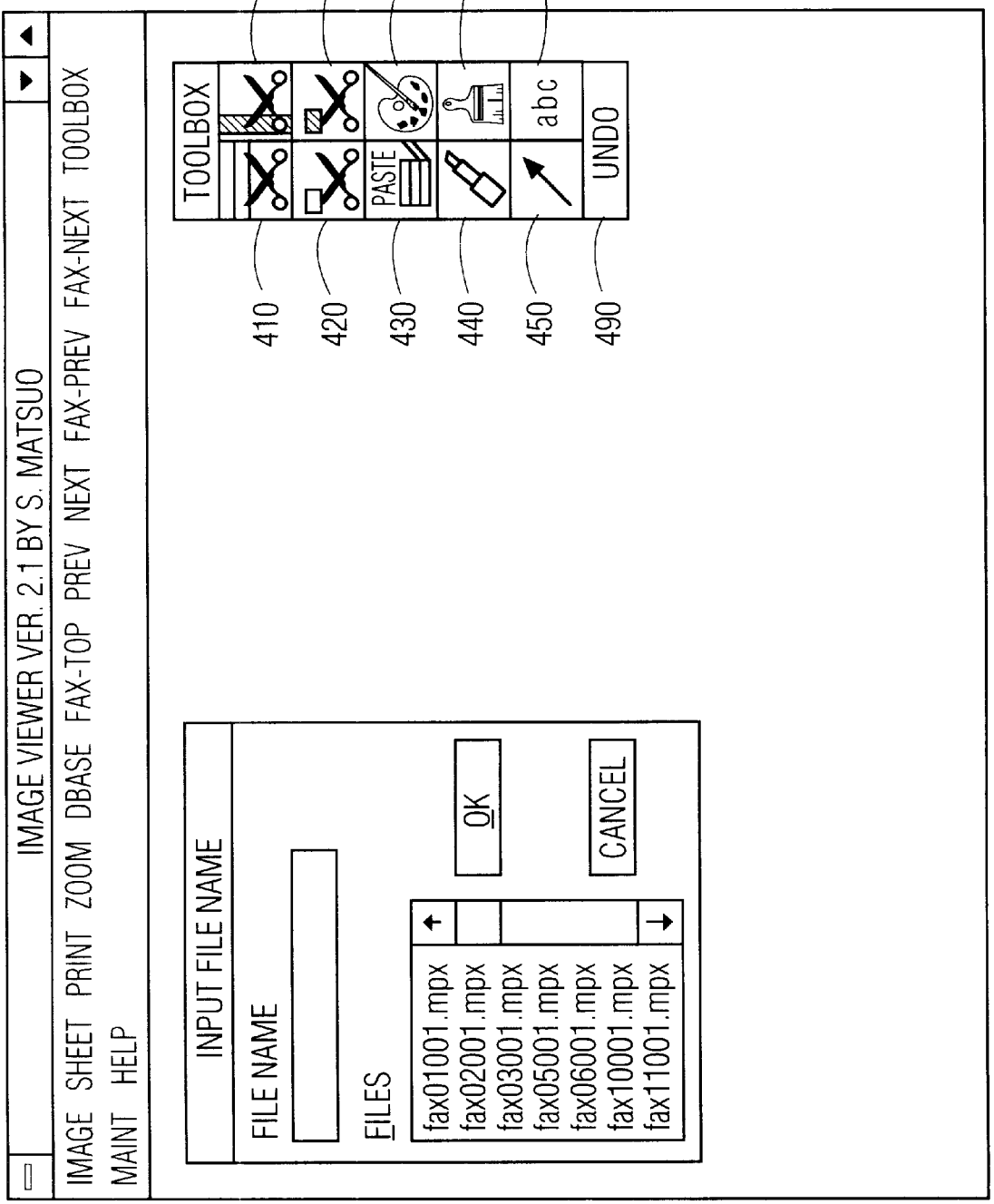
FIG. 9 is an explanatory drawing of a display on the display/processing program window when a file saved under an alias is selected at step 222 shown in FIG. 2.

The following describes operations to be performed instead of step S222 in FIG. 2 with reference to FIG. 9.

The CPU block 100 judges whether or not there are both a MAP file and a MPX file corresponding to a designated

TABLE 5

| Processing Item | | | | | | Object code | | | | | | | | | |
|---|---|---|---|---|---|---|---|---|---|---|---|---|---|---|---|
| 1 | 0002 (PAINT) | 0006 (CL = red) | 0223 (X1) | 0211 (Y1) | 037A (X2) | 0217 (Y2) | | | | | | | | | |
| 3 | 0004 (CHARACTER) | 0001 (CL = black) | 0155 (X1) | 0185 (Y1) | 019F (X2) | 019C (Y2) | 0017 (SZ) | 0030 (0) | 0035 (5) | 002F (/) | 0032 (2) | 0038 (8) | 002F (/) | 0039 (9) | 0031 (1) | 0000 |
| 4 | 0003 (Arrow-marked color line) | 0001 (CL = black) | 0170 (X1) | 017A (Y1) | 01DA (X2) | 0145 (Y2) | | | | | | | | | |

An item of processing to be undone shall be specified as follows:

If a range is designated after the UNDO icon 490 is clicked, the last processing item is canceled from among all processing items covering the designated range, in which case a judgment is formed as to whether to include a moved or copied image among objects to be processed, depending on whether or not corresponding moved or copied image comes within the designated range.
(4) If it is judged at step S212 that the message is HOLD, the contents of the transparency data buffer 142 are held on the local disk 150. The file name and directory of transparency data 152 must be the same as those of the corresponding source image, and only the file extender should be changed to MPX. If the same directory is not found on the local disk 150, a directory should be created in advance.

In this case, a judgment as to whether or not there is transparency data at step S222 shown in FIG. 2 can be formed by making a judgment as to whether or not the file name of a designated image and a directory with the extender MPX are present on the local disk 150.
(5) If it is judged at step S212 that the content of a message is END, the display/processing program window 121 is closed to terminate the operation of the image display/processing program (at step S299).
(6) If it is judged at step S212 that the input message is none of (1) to (5), control returns to step S212 and waits for input of a message.

Since in Embodiment 1, the file name of transparency data 152 has been equalized to the file name of images, only one processed image can be held in correspondence to each one source image.

image on the local disk 150, and goes to step S228 if either one is not present. If both files are present, the CPU block 100 reads the MAP file, displays a list of image titles (MPX file list) as FIG. 9 shows, selects an MPX file with the title of an image designated by a user, and goes to step S244.

From step S244 on, the CPU block 100 processes (at step S226) and displays (at step S228) the transparency data stored in the MPX file thus selected, whereby it is able to provide a user interface that appears as if a processed image were being held with the title of a processed image.

Figure 10:
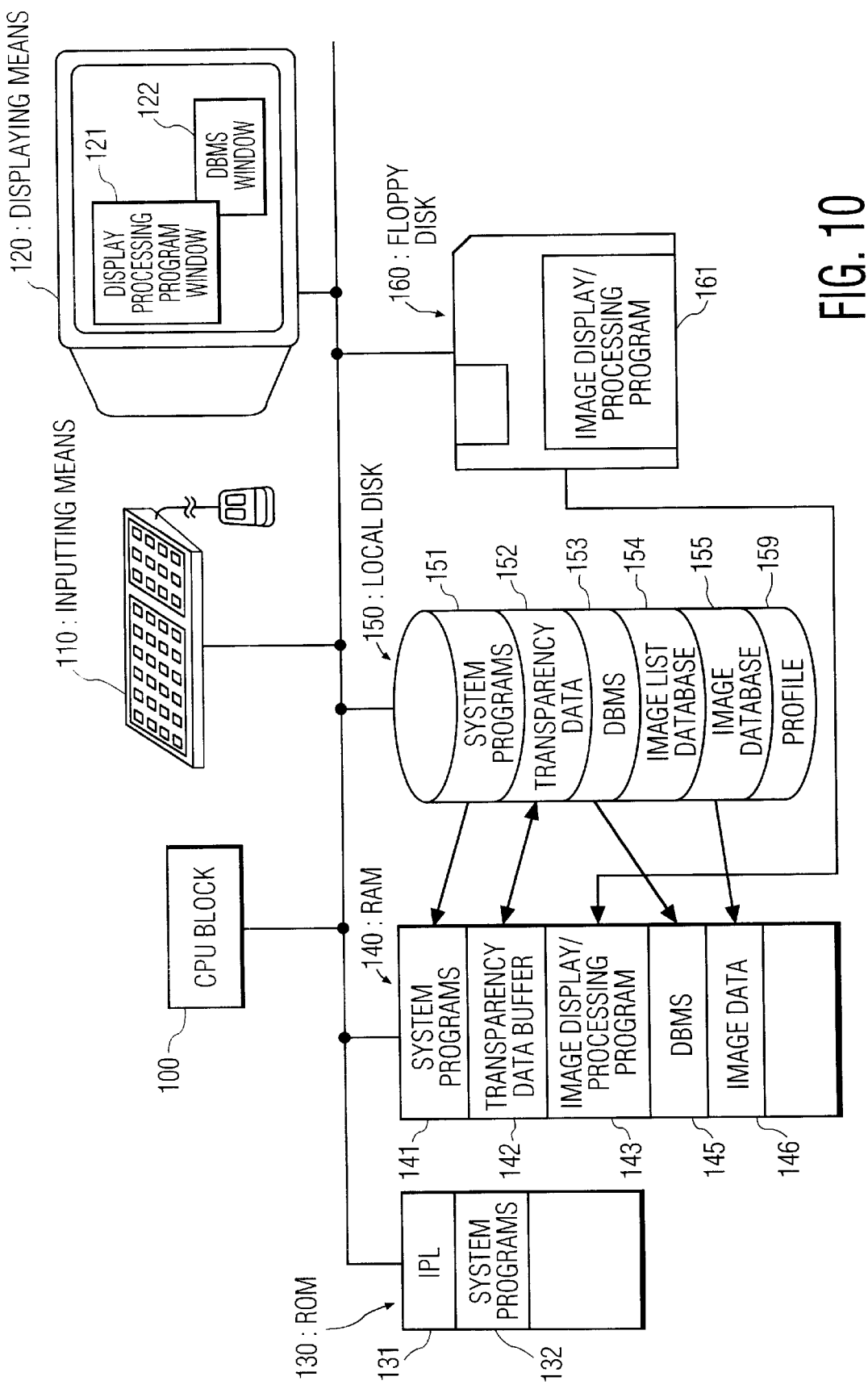
FIG. 10 is a block diagram of the hardware configuration of a standalone computer as an embodiment of this invention.

FIG. 10 shows the configuration of still another embodiment where this invention is applied not to a client server type computer but to a standalone computer. In this embodiment, the DBMS, image list database, and image database are stored in the local disk 150. Image data is input into the RAM 140 from the local disk 150, not by the communication means 170 as in Embodiments 1 and 2.

The other aspects of the configuration and behavior of Embodiment 3 are basically the same as those of Embodiments 1 and 2 described so far.

Thus, when this invention is applied to a standalone computer, it is in effect possible to prevent waste use of the storage capacity of the local disk 150 by processed images. Also, it is in effect possible to "undo" processing, similarly to the case in Embodiments 1 and 2.

As evident from the above, this invention enables reproduction of a processed image without storing such a processed image itself, inasmuch as a source image and processing content are stored separately in a source image file and a processing content file (transparent sheet) respectively, which are combined when a processed image is displayed. This advantage helps prevent waste of storage capacity with processed images.

Moreover, this invention enables reproduction of a processed image without storing such a processed image in a second information processor, inasmuch as a source image stored in a first information processor is transferred to a second information processor, wherein image processing instructions are input, processing content is stored, and images are processed. This advantage helps prevent waste of the storage capacity of the second information processor with processed images. Using source images stored in the first information processor as a database shared with more than one user, each user can personalize images by creating only processing data with the aid of the second information processor without directly altering these source images.

This invention enables display of a processed image even where a source image (unprocessed image) associated with a database is read, inasmuch as an image is processed according to its corresponding processing content if such processing content corresponding to the image to be read has been stored. Hence, processed images can be retrieved by source image retrieval using a DBMS.

This invention allows creation of an image when an instructed processing item has been undone, inasmuch as an item of processing content instructed to be undone is deleted from the processing content stored in advance and image processing is carried out according to the processing content after the deletion.

This invention enables storage of more than one kind of processing content corresponding to the title of a processed image without storing such a processed image, inasmuch as the title of a processed image is input and the title is stored in correspondence to said processing content. Moreover, any of a plurality of titled processed images can be selectively displayed without storing processed images, inasmuch as the title of an image is displayed and an image processed according to an item of processing content corresponding to a designated title is also displayed if it is judged that the processing content corresponding to the image to be read has already been stored.

This invention helps to cut down on the amount of transmission data and save on storage capacity by sending only a transparent sheet to another user linked to the LAN and obtaining a source image file from a database.

I claim:

1. An image processing system for storing a source image and modified versions of said source image, comprising:

means for storing a source image in a source image file;

means for storing processing content produced by image processing instructions in a processing content file separate from said source image file, said processing content in said processing content file, when applied to said source image, producing a modified image; and means for retrieving a copy of said source image from said source image file and for retrieving said processing content from said processing content file and for applying said retrieved processing content to said retrieved copy of said source image to produce said modified image for display, without modifying said source image stored in said source image file, wherein said source image file is permanently stored only remotely at a file server in a network and said processing content file is stored locally at a user location in said network in place of locally storing said modified image, a user retrieving said source image file from said file server and applying said processing content thereto to form said modified image whenever a display of said modified image is desired at said user location.

2. A method of storing a source image and modified versions of said source image, comprising the steps of:

storing a source image in a source image file;

creating processing content from image processing instructions, said processing content, when applied to said source image, producing a modified image;

storing said processing content in a processing content file separate from said source image file;

retrieving a copy of said source image from said source image file and said processing content from said processing content file; and applying said retrieved processing content to said retrieved copy of said source image to produce said modified image for display, without modifying said source image stored in said source image file, wherein said source image file is permanently stored only remotely at a file server in a network and said processing content file is stored locally at a user location in said network instead of locally storing said modified image, a user retrieving said source image file from said file server and applying said processing content thereto to form said modified image whenever a display of said modified image is desired at said user location.

* * * * *